United States Patent [19]

Morris et al.

[11] Patent Number: 4,647,210
[45] Date of Patent: Mar. 3, 1987

[54] CHLORINE ANALYSIS USING FIBER OPTICS

[75] Inventors: Thomas E. Morris, Lake Jackson; Tarver G. Snedecor, Jr., Angleton, both of Tex.

[73] Assignee: The Dow Chemical Company, Midland, Mich.

[21] Appl. No.: 745,775

[22] Filed: Jun. 17, 1985

[51] Int. Cl.$^4$ .............................................. G01N 21/85
[52] U.S. Cl. .................................. 356/410; 356/414; 356/418; 356/419
[58] Field of Search ............... 250/339, 343, 573, 576, 250/575; 356/409, 410, 411, 412, 414, 416, 418, 419, 425, 432, 436, 437, 439

[56] References Cited

U.S. PATENT DOCUMENTS

| | | | |
|---|---|---|---|
| 3,740,155 | 6/1973 | Keller et al. | 356/409 |
| 3,864,044 | 2/1975 | Lyshkow | 356/436 |
| 3,899,688 | 8/1975 | Perieres | 250/576 |
| 4,152,073 | 5/1979 | Zimmerman | 356/436 |
| 4,534,651 | 8/1985 | Minikane | 356/409 |
| 4,567,366 | 1/1986 | Shinohara | 250/343 |

FOREIGN PATENT DOCUMENTS

| | | | |
|---|---|---|---|
| 2133797 | 1/1973 | Fed. Rep. of Germany | 356/436 |
| 0146098 | 1/1981 | Fed. Rep. of Germany | 356/437 |
| 7418510 | 12/1975 | France | 356/432 |

OTHER PUBLICATIONS

Hawes et al., *Anal. Chem.*, vol. 23, No. 3, 3/16/51, p. 503.

*Primary Examiner*—F. L. Evans
*Assistant Examiner*—Joel L. Harringa
*Attorney, Agent, or Firm*—A. C. Ancona

[57] ABSTRACT

For measurement of chlorine concentration in a process stream, an improved device is set forth measuring light transmission in a selected frequency range. The preferred embodiment uses a light source, a light filter and an optical fiber extending to a pipe or other vessel with flowing chlorine. The light is transmitted from a lens system to another lens system and into a second optical fiber. The second fiber extends to a measuring device.

4 Claims, 2 Drawing Figures

CHLORINE ANALYSIS USING FIBER OPTICS

BACKGROUND OF THE DISCLOSURE

The present apparatus is directed to a system for measuring the concentration of chlorine flowing in a process stream. Chlorine is a strong reactant which is handled in process plants only in specifically contructed pipes and conduits. Because of its strong chemical nature, it typically is contained under specially made devices with safe guards to prevent escape. The strong chemical activity of chlorine makes it difficult to obtain measurements of chlorine. That is, it is not quite so easy to obtain access to the chlorine to make flow or volume measurements as might be required. A particularly important requirement in the handling of chlorine in large processing plants where chlorine is either manufactured or used is measurement of the concentration of chlorine. The process stream typically includes some kind of conduit connecting some source of chlorine either with a storage tank or alternatively with a process using the chlorine. Attempts have been made in the past to make such measurements. One such device is set forth in U.S. Pat. No. 2,286,985. This device sets forth a phototube arrangement. A more recent device is a smoke detector utilizing cylindrical light transmitting rods of about ½" in diameter. This is shown in U.S. Pat. No. 3,976,891. Two U.S. patents by Zimmerman (U.S. Pat. Nos. 3,968,006 and 4,152,073) are also directed to chlorine measurement systems. A laser transmitted along a pipe is set forth in U.S. Pat. No. 4,421,408. It is believed that none of these references either singly or collectively set forth the improved system of this disclosure for measuring chlorine concentration.

This apparatus incorporates a means for measuring concentration without difficulties arising from invasion of the pipe where the chlorine flows. Rather, chlorine attack on the measuring apparatus is limited by the use of an impervious lens. The lens is particularly able to prevent unwanted entry of chlorine or damage arising from it. Further, a comparative technique is utilized wherein light of two separate wavelengths is transmitted through the chlorine. A particular wavelength is selected where the light is absorbed by the chlorine while another wavelength is selected where chlorine absorption is substantially nil. The second wavelength light is used as a reference. This reference is particularly valuable to remove errors which might arise as a result of lamp aging. It also overcomes errors that might occur with degradation of the light transmission path over a period of time. To the degree that degradation does occur, it impacts equally both wavelengths so that the reference is likewise degraded. This enables relative measurements against the reference whereby aging and degradation factors are substantially eliminated.

A particularly important advantage of the present apparatus is the positioning of the light source and analyzing equipment remote from the pipe or conduit in which the chlorine is flowing. Mounting immediately on the pipe is not required. If convenient, it certainly can be mounted on the pipe but the equipment can likewise be mounted elsewhere. The equipment incorporates a light source which must be periodically changed. For this reason, it may be appropriate to locate the light source convenient for personnel and to extend optical fibers from the lamp to the pipe or vessel. This enables a measure of adaptability and improves the mounting of the apparatus.

With the foregoing advantages in view, the present apparatus is briefly summarized as a chlorine concentration measuring system including a housing having a light source therein emitting light in a specified spectrum. A rotating optical filter is included. Preferably, it passes two wavelengths. One wavelength is selected to substantially pass through the chlorine. The second wavelength is preferably about 3600 angstroms which wavelength is absorbed by chlorine. That is, the chlorine is opaque to this wavelength by an amount or in a measure determined by the concentration of chlorine. The light is emitted, passed to the filter, and travels along an optical fiber. The optical fiber is tipped by a sapphire lens in a housing mounted in the wall of the pipe for projecting a beam of light across the pipe. A similarily mounted optical fiber on the opposite side protected by a similar sapphire lens receives the light beam. The light passing through the chlorine is then transmitted through the optical fiber to a photometric detector. The signal is supplied to a processor for conversion into calibrated data. As appropriate, this can be connected with a recorder.

BRIEF DESCRIPTION OF THE DRAWINGS

So that the manner in which the above-recited features, advantages and objects of the present invention, as well as others which will become apparent, are attained and can be understood in detail, a more particular description of the invention, briefly summarized above, may be had by reference to the embodiments thereof illustrated in the appended drawings, which drawings form a part of this specification.

It is to be noted, however, that the appended drawings illustrate only typical embodiments of this invention and are not to be considered limiting of its scope, for the invention may admit to other equally effective embodiments.

DETAILED DESCRIPTION OF THE PREFERRED EMBODIMENT

Figure 1:
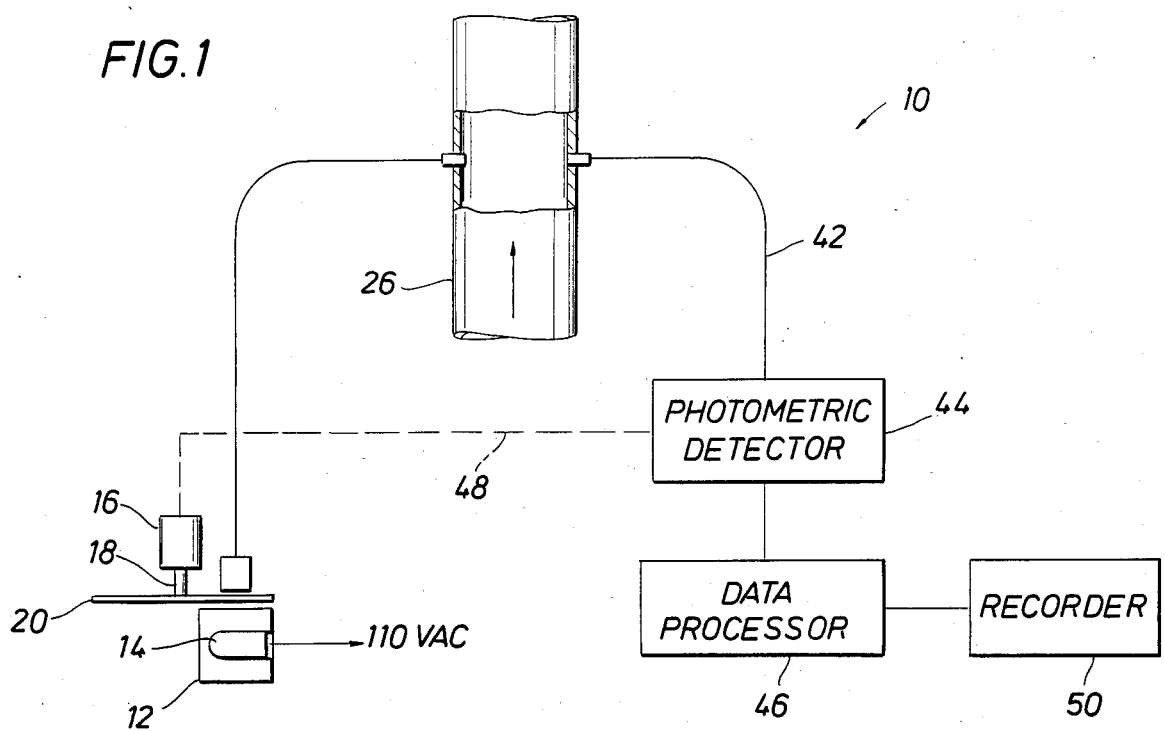
FIG. 1 is a schematic block diagram showing the chlorine concentration measuring apparatus of this disclosure connected by optical fibers to a pipe or vessel having chlorine therein.

Attention is first directed to FIG. 1 of the drawings where the numeral 10 identifies the chlorine concentration measuring apparatus of this disclosure. The chlorine concentration measuring apparatus includes a closed housing 12 surrounding a lamp 14. The lamp is connected with a suitable power source for the lamp and is left on so long as measurements are required. The lamp emits light across a specified spectrum. In the light spectrum of the lamp, two wavelengths are selected. One of the wavelengths is preferably 3600 angstroms. At this wavelength, chlorine absorbs the light and hence provides a measure of opaqueness which varies with concentration. As will be understood, other wavelengths may be selected but this wavelength has relative greater sensitivity. Deviation from a precise frequency of 3600 angstroms to a less sensitive wavelength is permitted if determining is desirable. For instance, light at a wavelength of 3500 angstroms might suffice for transmission across a fairly wide spacing. However, it must be understood that variations from the preferred frequency of 3600 angstroms reduces sensitivity in the system.

The second wavelength can be any wavelength which is relatively free of attenuation from the chlorine. For instance, wavelengths of about 5000 to 10,000 angstroms are substantially free of chlorine attenuation. This range of wavelength is preferred because attenuation by other components in the stream is optimum.

A motor 16 having a shaft 18 rotates a wheel 20. The wheel or disc is circular and made of an opaque material having two or more windows in it. The windows are covered by transparent members capable of passing light at the selected wavelengths. They are transparent at the selected wavelengths and opaque to the excluded wavelengths. Hence, one of the windows is preferably transparent to 3600 angstroms. The other window is preferably transparent to some wavelength within the range previously mentioned.

Figure 2:
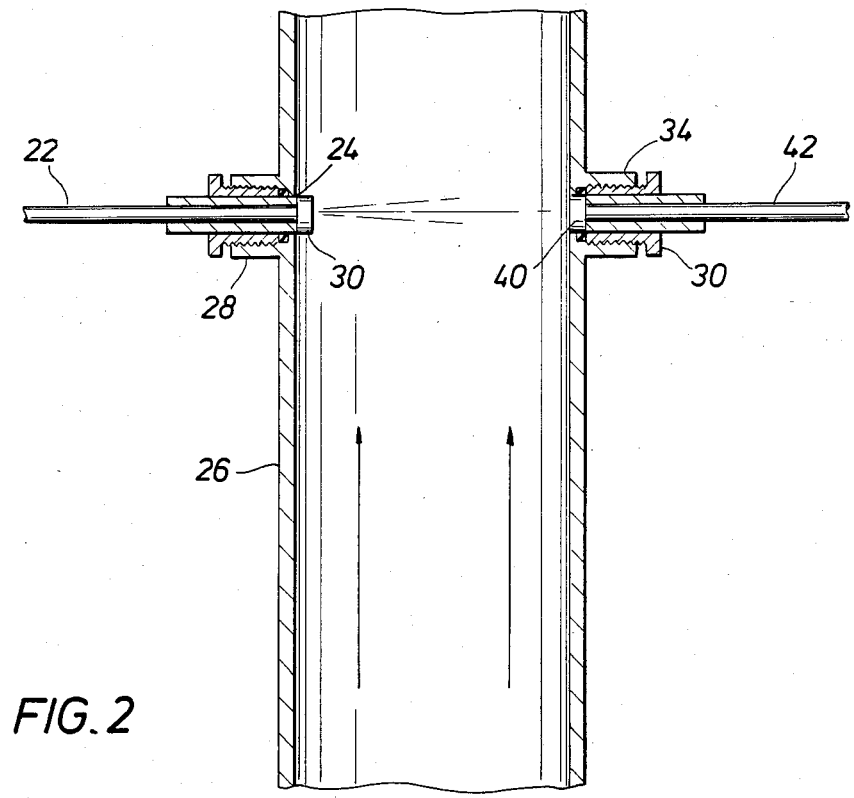
FIG. 2 is an enlarged view showing details of construction of the optical fiber tips including sapphire lenses mounted in the pipe for transmission of light across the pipe.

Light from the source 14 is thus passed from the rotating disc or wheel 20 and enters an optical fiber 22. This light travels along the optical fiber to the structure better shown in FIG. 2 of the drawings. There, the fiber 22 is received in a threaded tubular member 24. The member 24 has external threads for threading to a mounting on the pipe 26. The mounting is identified by the numeral 28. The tubular member 24 terminates at sapphire lens 30. The sapphire lens 30 is positioned adjacent the end of the optical fiber 22 permitting light to be transmitted through the end of the optical fiber and through the lens 30. The lens is preferably circular, having a diameter typically in the range of about $\frac{1}{8}''$ to about $\frac{1}{4}''$. It is relatively thick to resist pressure loading which may occur in the pipe 26. It is not uncommon to have pressure in excess of 1000 psi in vessels handling gaseous chlorine. Moreover, suitable seals are included to prevent leakage along threads between the mounting member 28 and the tubular member 24.

The threaded mounting 28 is aligned opposite a similar threaded mounting 34. It also receives a tubular member 36 terminating in a similar sapphire lens 40. The lens 40 is directly opposite the lens 30. The tubular member 36 encloses an optical fiber 42. The optical fiber 42 shown in FIG. 1 extends to a photometric detector 44. This in turn is connected with a data processor 46. That is connected with a recorder 50 to record data and provide an indication of concentration of chlorine.

The detector 44 responds to light transmitted at the two wavelengths across the pipe 26. Recall that two wavelengths are utilized; one wavelength is readily absorbed by the chlorine while the other wavelength is preferably selected because it is transparently transmitted by the chlorine. The photometric detector thus provides an output signal indicative of light intensity. One light intensity is to obtain the reference wavelength while the second light intensity is a function of concentration of chlorine in the pipe 26. This data is provided to the data processor 46 which converts these measurements along with a suitable scale factor into a measure of chlorine concentration.

Consider operation of the present apparatus. Assume that the light wavelengths are 3600 and 7000 angstroms. The disc 20 is rotated to provide these wavelengths into the optical fiber 22. The speed of rotation is not a critical factor and can be varied widely. Light pulses are thus transmitted through the optical fiber 22. The fiber 22 can be of any suitable length so that the lamp 12 can be conveniently located. Moreover, the pipe 26 may be at a remote location, perhaps many feet away. In any event, the portion of the equipment which includes the light source 12 and all the equipment at the end of the optical fiber can be located at a remote location whereby the optical fiber 22 extends to the pipe 26. The tip of the optical fiber is received in the tubular sleeve 24 and directs light through the lens 30. For convenience of servicing, the tubular member 24 can be demounted by unthreading. Separately, the optical fiber 42 is connected in a similar fashion with the threaded member 36. Being opposite one another, each has a view of the other. The optical fibers are aligned by the tubular sleeves directly across from one another. The light is directed from the lamp source through the optical fiber 22 and passes across the pipe 26. The light enters the optical fiber 42 and is then transmitted to the photometric detector 44.

Calibration of the system relative to the reference should be considered. Assume that the equipment is switched on and left operative for many months. During this interval, the lamp will age. Alternatively, chlorine may foul the equipment and form a coating over the lenses. This might be noted at the detector 44 in the form of a reduction in reference output by perhaps 25% to consider one example. The reference transmission is observed at the photometric detector. As it provides a decreased signal, the decrease provides reference modification for the other wavelength. By use of suitable calibration standards placed between the two lenses in the pipe 26, calibration in terms of concentration of chlorine can then be implemented. This is adjusted so that lamp aging or fouling is removed as an error source.

As noted in FIG. 1, the motor 16 is synchronized by electronic or mechanical means to the photometric detector 44. This synchronization enables the detector to know which of the two wavelengths is being transmitted to it. This enables the detector 44 to segregate the two signals received at the detector, one being a reference and the other being the variable as a function of chlorine concentration. Conveniently, all of the equipment shown in FIG. 1 can be installed at one location remote from the equipment connected with the pipe 26. This would then enable the extention of the optical fibers 22 and 42 by substantial distance to the pipe.

While the foregoing is directed to the preferred embodiment, the scope thereof is determined by the claims which follow.

What is claimed is:

1. Apparatus for determining concentration of chlorine in a process stream confined in a flow conduit comprising:
    (a) light means forming a light spectrum which spectrum includes light at a specified fequency, the frequency being selected to match a characteristic frequency response of the flowing chlorine;
    (b) a first optical fiber of specified length having two ends, one end being exposed to said light means to receive light therefrom, therebeing a second end which is adapted to emit light at the specified frequency;
    (c) first mounting means for positioning the second end of said fiber at a location in a flowing stream of chlorine for projecting light across the flowing stream of chlorine;

(d) a second optical fiber having two ends adapted to receive light at one of said two ends, and wherein said second fiber is able to pass light at the selected frequency;

(e) second mounting means for positioning a first end of second fiber to receive light from the second end of the first fiber across the flowing stream of chlorine wherein the flowing chlorine varies the amount of light transmitted between said first and second fibers;

(f) light intensity measuring means connected to the second end of said second fiber for receiving light originating from said light means wherein the light intensity is varied by the flowing stream of chlorine;

(g) a frequency selective filter and means repetitively inserting and removing said filter to interrupt light from said light means to assure that alternate frequencies of light are transmitted across flowing chlorine wherein:
  (1) one alternating light frequency is selected where flowing chlorine is transparent;
  (2) wherein the other alternating light frequency is absorbed by the flowing chlorine;

(h) wherein said measuring means observes said alternate light frequencies for obtaining separate measures at the frequencies of observed light intensity; and (i) wherein both of said first and second mounting means include a protective lens exposed to the flowing chlorine, said lenses being transparent to the alternating light frequencies from said light means, said lenses being resistant to attack by flowing chlorine, and said lenses being mounted to protect the respective ends of said optical fibers from the flowing chlorine, and wherein said optical fiber ends are aligned to transmit light through the flowing chlorine.

2. The apparatus of claim 1 wherein said light means forms light which passes through first and second filters for admission into said first optical fiber.

3. The apparatus of claim 2 including means for synchronizing the transmission of the alternate frequencies through said optical fibers with operation of said light intensity measuring means to enable said light intensity measuring means to provide an output signal indicative of light intensity of the alternating frequencies transmitted through said optical fibers.

4. The apparatus of claim 3 wherein said protective lenses include an exposed lens surface of sapphire.

* * * * *